United States Patent [19]

Rei et al.

[11] Patent Number: 5,229,124

[45] Date of Patent: Jul. 20, 1993

[54] MICROBICIDES IMMOBILIZED IN WATER SOLUBLE THERMOPLASTIC RESINS AND AQUEOUS DISPERSIONS OF MICROBICIDES PREPARED THEREFROM

[75] Inventors: Nuno M. Rei; Lawrence P. Grant, both of Boxford; Roger G. Hamel, Methurn, all of Mass.

[73] Assignee: Morton International, Inc., Chicago, Ill.

[21] Appl. No.: 763,886

[22] Filed: Sep. 20, 1991

Related U.S. Application Data

[63] Continuation of Ser. No. 503,359, Apr. 2, 1990, abandoned.

[51] Int. Cl.⁵ .............................................. A61K 47/30
[52] U.S. Cl. .................................. 424/409; 424/419; 424/497; 514/772.3; 514/785
[58] Field of Search .................. 424/81, 78, 409, 419, 424/497; 514/785, 772.3

[56] References Cited

U.S. PATENT DOCUMENTS

| B1 4,086,297 | 6/1988 | Rei et al. | 524/330 |
|---|---|---|---|
| Re. 29,409 | 9/1977 | Yeager | 424/78 |
| 1,971,662 | 8/1934 | Schmidt et al. | 260/2 |
| 2,844,570 | 7/1958 | Broderick | 260/91.3 |
| 2,990,398 | 6/1961 | Inskip et al. | 260/91.3 |
| 3,033,841 | 1/1958 | Germain | 260/89.1 |
| 3,299,566 | 1/1967 | MacMullen et al. | 47/1 |
| 3,425,979 | 7/1963 | Monaghan et al. | 260/33.2 |
| 4,086,297 | 4/1978 | Rei et al. | 524/94 |
| 4,155,742 | 5/1979 | Sakurai et al. | 71/67 |
| 4,369,281 | 1/1983 | Zimmermann et al. | 524/379 |
| 4,469,837 | 9/1984 | Cattaneo | 524/388 |
| 4,661,528 | 4/1987 | Rei et al. | 523/122 |
| 4,663,077 | 5/1987 | Rei et al. | 523/122 |
| 4,663,359 | 5/1987 | Rei | 521/85 |
| 4,758,609 | 7/1988 | Rei et al. | 524/109 |
| 4,789,692 | 12/1988 | Rei et al. | 523/122 |
| 4,795,641 | 1/1989 | Kashdan | 424/438 |
| 4,888,175 | 12/1989 | Burton, Jr. et al. | 424/409 |
| 4,891,391 | 1/1990 | McEntee | 524/563 |

FOREIGN PATENT DOCUMENTS 60-190723 9/1985 Japan .
2095558 10/1982 United Kingdom .

OTHER PUBLICATIONS

Chem. Ab. vol. 94:20412e.

*Primary Examiner*—Thurman K. Page
*Assistant Examiner*—Peter F. Kulkosky
*Attorney, Agent, or Firm*—Wayne E. Nacker; Gerald K. White

[57] ABSTRACT

Solid solutions comprise a water-soluble thermoplastic resin and a microbicide dissolved therein. These solutions may be added to a rigid thermoplastic resin composition to impart biocidal characteristics thereto. If the microbicide is water-insoluble, the solid solutions may be used to prepare stable dispersions of the microbicide. The solutions also provide for slow release of a microbicide or as a vehicle for providing microbicide to an aqueous solution.

19 Claims, No Drawings

MICROBICIDES IMMOBILIZED IN WATER SOLUBLE THERMOPLASTIC RESINS AND AQUEOUS DISPERSIONS OF MICROBICIDES PREPARED THEREFROM

This is a continuation of copending application Ser. No. 07/503,359 filed on Apr. 2, 1990, now abandoned.

The present invention is directed to solid microbicide concentrates in which microbicide are immobilized in water-soluble resins. Such concentrates are particularly useful as additives to solid resins as a means of imparting biocidal activity thereto. In addition, a concentrate, in which a water-insoluble microbicide is dissolved in a water-soluble resin, can be added to water or an aqueous solution to prepare a microdispersion of the microbicide. Such a microdispersion is useful, for example, for treating yarns or fabric to impart biocidal activity thereto.

BACKGROUND OF THE INVENTION

It is known to protect various thermoplastic resin compositions against fungal or bacterial attack by incorporating a microbicide therein to prevent the deterioration of articles formed from the resin compositions. Microbicide inhibit growth of bacteria or fungi by acting upon the cell wall or upon cell proteins, e.g., by attacking disulfide bonds. In order for the microbicide to be effective in the resin composition, it is necessary that it be compatible with the components of the resin composition and be uniformly dispersible in the resin composition. The microbicide must be carried by the resin composition in a manner that it remains biologically active against microorganisms, and, in particular, must be available at the surfaces, including internal pore surfaces. Incorporation of microbicides in resin compositions is generally effective only in compositions in which the microbicide is able to slowly migrate to the surfaces. In some cases, the microbicide migrates slowly through amorphous regions of the polymer. In other cases, biocide migration is facilitated by plasticizers which are included along with the polymeric resins in end-use resin compositions. As the microbicide at the surfaces in used up through action against microorganisms, additional microbicide migrates to the surfaces. Although a microbicide may be a highly toxic chemical, its low concentration in the end-use product and its retention by the resin composition ensures that the microbicide in the end-use product poses no hazard to humans or animals.

Microbicides must be available in a form that is readily dispersible into the formulation mix from which the end-use resin composition is fabricated. The powdered or crystalline form in which many useful microbicides are commercially available are readily dispersible; however, at the site of mixing, powdered or crystalline microbicides pose a substantial environmental and health hazard if powder or crystal fines are dispersed into the atmosphere. Furthermore, powder, or powdered fines, if dispersed into the atmosphere, represent a potential explosive hazard.

Recognizing the toxicity problem of microbicides in powder or crystalline form, U.S. Pat. No. Re. 29,409 teaches dissolving microbicides in liquid solvents which may be added to the formulation mixture from which the end-use resin compositions are fabricated. Although liquid dispersions may be safely used at the site of preparing end-use resin compositions, careless use or disposal of the liquids may still pose environmental and health hazards.

U.S. Pat. No. 4,086,297 issued Apr. 25, 1978 to Rei, et al., the teachings of which are incorporated herein by reference, describes solid thermoplastic microbicide resin concentrates containing immobilized microbicides. These solid microbicide resin concentrates contain relatively high concentrations of microbicides and may be added to the formulation mixtures from which the end-use resin compositions are prepared in an amount sufficient to provide the desired end-use microbicide concentrations. The solid microbicide resin concentrates, which are typically provided in the form of small pellets, can be handled freely, posing substantially no health or environmental threat. Such pellets are even safe for direct skin contact. Although microbicides are sufficiently immobilized and inactive in the solid microbicide resin concentrates, in softer end-use resin compositions, the low concentration microbicides at the surface have biological activity, and gradual and continuous migration to surfaces ensures continuous biological activity. Where practical, a solid microbicide resin concentrate represents a preferred manner of providing a microbicide to producers of end-use thermoplastic products.

U.S. Pat. No. 4,789,692, the teachings of which are incorporated herein by reference, discloses blends of polymers and also copolymers and terpolymers that are particularly suitable for carrying concentrated levels of microbicides into particular thermoplastic resins.

In order that inclusion of a microbicide impart biocidal activity to an end-use product, the microbicide must be available at the surface to act against microbial growth. In a flexible end-use composition, which comprises a thermoplastic resin and a plasticizer, the plasticizer commonly provides the transport mechanism for continual replenishment of incorporated microbicide to the surface of the end-use article. A typical product of this nature is a polyvinyl chloride (PVC) shower curtain which contains substantial amounts of plasticizer and sufficient microbicide to protect the shower curtain from microbial attack for an extended period of time.

On the other hand, rigid polymeric materials may be afforded substantially no protection by the inclusion of microbicides because the incorporated microbicide does not migrate to the surface where it is available to act against microbial organisms. An example of this is rigid PVC, such as that for siding of houses. Unlike flexible, plasticized PVC compositions, rigid, non-plasticized PVC is not particularly subject to degradation by microbial attack. Nevertheless, microbial growth on the surface of such rigid polymeric material is undesirable, particularly from an aesthetic standpoint.

It is a primary object of the invention to provide solid concentrates of microbicides-in-resins that can be used to provide biocidal activity to rigid thermoplastic resins. Other objects and advantages will become more fully explained in the following description of the invention.

SUMMARY OF THE INVENTION

In accordance with the invention, there are provided concentrates of microbicides in water-soluble thermoplastic resins. These concentrates can be added to rigid thermoplastic resin compositions and impart biocidal activity thereto so as to inhibit microbial growth on the surfaces thereof.

A surprising and unexpected alternative use of a concentrate, in particular such a concentrate in which a water-insoluble microbicide is dissolved in a water-soluble resin, is in the preparation of a microdispersion of the microbicide in an aqueous medium. Adding the concentrate to an aqueous medium dissolves the water-soluble resin and precipitates particles of the microbicide that are sufficiently minute to form a stable dispersion in the aqueous medium. Such a dispersion is useful, for example, in treating textiles to impart biocidal activity thereto.

DETAILED DESCRIPTION OF CERTAIN PREFERRED EMBODIMENTS

One aspect of the present invention is directed to concentrates of microbicides in water-soluble thermoplastic resins, which concentrates are used to carry microbicides into end-use resin compositions. It is found that water-soluble thermoplastic resins promote mobility of microbicides in end-use resin compositions, promoting migration of the microbicides to surfaces (including pore surfaces) of the end-use resin compositions. It is particularly difficult to protect surfaces of rigid or glassy thermoplastic resin compositions from surface microbial growth by incorporation of microbicides, because incorporated microbicides tend to be immobilized in such compositions. When the microbicide at the surface of such a composition is depleted, it is not replenished by migration of microbicide incorporated internally, or at least not at a sufficient rate. Thus, by use of the water-soluble thermoplastic resins as microbicide carriers in accordance with the invention, thermoplastic resin compositions, which heretofore could not be adequately protected by incorporating microbicides, may now be protected. Concentrates according to the invention have been shown to impart biological activity to rigid compositions of polyethylene terephthalate (PET) acrylonitrile-butadiene-styrene polymer (ABS), polyvinyl chloride (PVC), polyvinylidine chloride (PVDC), polycarbonate and polystyrene.

Rigid or glassy thermoplastic resin compositions are generally those having a glass transition temperature above room temperature, e.g., above about 25° C. However, whether or not microbicide will be migratory or non-migratory in an end-use resin composition or whether, if migratory, at any appreciable rate, will depend upon a variety of factors, including the chemical composition of the resin or resins and the additives to the end-use resin composition, such as plasticizers, flow-control agents, fillers, etc. In any case, it is believed that the water-soluble thermoplastic carrier resins used in accordance with the present invention generally promote microbicide migration in end-use thermoplastic resin compositions. Thus, while a particularly important application of the concentrates is to enable solid or glassy thermoplastic resins to be protected by incorporated microbicides, the concentrates have broad applications to thermoplastic resin compositions. For example, a non-rigid, thermoplastic, end-use resin composition for which a short life-span is anticipated, e.g., a garbage bag, may require less total amount of microbicide if the migration rate of the microbicide is enhanced.

By aqueous-soluble thermoplastic resin is meant a thermoplastic resin which is soluble to at least about 1 gm. per 100 ml of water at 25° C. and preferably at least about 5 gm. per 100 ml of water at 25° C.

In order to be useful as carriers of microbicides, it is necessary that the resins be thermoplastic, and in this respect, the carrier resins must each melt at a temperature below its decomposition temperature. Concentrates according to the present invention are prepared by melt-blending the carrier resins and the microbicides. Furthermore, to be useful as a carrier in association with any end-use thermoplastic resin composition, the carrier resin should be stable to degradation at the processing temperature of the end-use thermoplastic resin composition.

In selecting a water-soluble resin as a carrier for a particular microbicide into an end-use resin composition, an important criteria is that the resin be capable of solubilizing a high concentration of the particular microbicide. In most cases, the addition of the water-soluble carrier resin is considered to be an undesirable addition to the rigid thermoplastic resin or at least imparts no advantageous properties to the end-use thermoplastic resin composition other than facilitating migration of the microbicide. To minimize levels of water-soluble resin added to the end-use resin composition, it is therefore generally considered that the higher the concentration of microbicide in the water-soluble carrier resin, the better. Of course, sufficient water-soluble resin must be added to the end-use resin composition to facilitate migration of the microbicide to the surface of the end-use resin composition during the life of the end-use product; however, solubility of the microbicide in the water soluble resin is generally the limiting factor.

It is usually necessary only that the microbicide be soluble in the molten water-soluble carrier resin. Depending upon the particular resin, the particular microbicide and the concentration, the concentrate in solid form may have the microbicide still fully dissolved in the solidified resin. However, it is permissable for many applications that the microbicide recrystallize to some extent upon solidification of the water-soluble carrier resin. In such case, the crystals of microbicide which form will be of very small size and will distribute evenly throughout an end-use resin composition or will be of a size suitable for other applications of the present invention hereinafter discussed.

A concentrate in accordance with the invention should contain at least about 20 times the concentration of microbicide that is to be present in the end-use thermoplastic resin composition, preferably at least about 100 times the end-use concentration. Depending upon the microbicide, the concentrate may contain up to 1000 times the end-use concentration. The concentrate is added to the end-use resin in an amount sufficient to provide the desired concentration of microbicide to the end-use product. Thus, for example, if the concentrate contains 100 times the end-use concentration of microbicide, it will be added to the thermoplastic resin of the end-use composition at a weight ratio of 1:99. The end-use concentration is that required in the end-use resin composition to prevent microbial growth thereon. The end-use concentration will vary widely, depending upon the particular microbicide used; however, selection of an appropriate end-use concentration is believed to be within the skill of one with ordinary skill in the art, particularly with reference to published activity levels of various microbicides.

End-use concentrations of several commercially-available microbicides in various types of resins are given in the table below:

| Active Ingredients | Applications/Use Levels | | | | | |
|---|---|---|---|---|---|---|
| | Vinyl | Olefins | TPU | PU Foam | EVA | Nylon |
| OBPA | 0.03 to 0.05% | 0.05 | .05 | .05 | 0.05 | 0.05 |
| T-129 | .25% | UNK | 0.25 | — | — | NA |
| Irgasan (Ciba Geigy) | NA | 0.1–0.5% | UNK | UNK | 0.05 | 0.05% |
| Kathon-893 (Rohm & Haas) | 2–4 phr | 0.05% | UNK | UNK | 0.5% | NA |
| Vancide PA (R. T. Vanderbilt) | 0.5% | NA | UNK | UNK | 0.5% | NA |
| Daconil 2787 (SDS Biotech) | 0.5 to 1% | UNK | UNK | UNK | UNK | |
| Preventol (Bayer) | 0.25 to 0.5% | UNK | UNK | UNK | UNK | UNK |
| TBZ (Merck/ Carbonl) | >0.25% | NA | UNK | UNK | NA | NA |
| Zinc omadine (Olin) | 0.2% | UNK | UNK | UNK | UNK | UNK |

The water-soluble thermoplastic resin is further selected according to the primary thermoplastic resin so that the water-soluble resin has minimal negative effects on the properties of the primary thermoplastic resin composition. In this regard, it may be advantageous that the water-soluble thermoplastic resin be chemically similar to the primary thermoplastic resin to which it is to be added.

Currently preferred water-soluble resin carriers are resins based primarily upon polyvinyl alcohol (PVA). Polyvinyl alcohols are hydrolysis products of polyvinyl acetate or another polyvinyl ester. Polyvinyl alcohols, without modification, tend to be non-thermoplastic, generally having decomposition temperatures below their melting points. However, polyvinyl alcohol T-M based resin compositions may be either externally or internally plasticized so as to exhibit thermoplastic properties. It is known for example to plasticize PVA with such plasticizers as polyethylene glycol, glycerol and neopentyl glycol and thereby give PVA compositions thermoplastic properties. Such externally plasticized PVA resins are described, for example, in U.S. Pat. Nos. 3,425,979 and 4,469,837, the teachings of which are incorporated herein by reference. PVA copolymers and graft polymers, such as those described in U.S. Pat. Nos. 2,990,398, 1,971,662, 2,844,570, 3,033,841 and 4,369,281, the teachings of which are incorporated herein by reference, also exhibit thermoplastic properties. A currently preferred internally plasticized PVA-based resin is a copolymer of vinyl alcohol and (alkyleneoxy)acrylate described in U.S. Pat. No, 4,618,648, the teachings of which are incorporated herein by reference. Such resins are sold under the trademark Vinex by Air Products.

Furthermore, it is desirable that the water-soluble resin be extrudable as a means of forming pellets of the concentrate. The microbicide and water-soluble resin are blended in the extruder above the softening point of the water-soluble resin, whereupon the microbicide is dissolved in the resin. Upon cooling, a solid solution (or suspension of micro crystals) of microbicide-in-resin results. Typically, the concentrates are extruded as strands and divided into pellets as they solidify.

The solid concentrates, like solid concentrates heretofore described, immobilize the toxic microbicide in a manner which is inherently safe to handle, as least greatly so relative to powdered microbicides.

The concentrates, e.g., in pellet or ground particulate form, are added to a thermoplastic resin in the conventional manner. Typically, concentrate pellets and fragmented primary thermoplastic resin are admixed along with optional additional additives in an extruder and the resin composition extruded at an appropriately elevated temperature. The end-use resin composition which results has sufficient microbicide to protect it from microbial growth and sufficient water-soluble resin to facilitate migration of the microbicide so as to provide microbicide to the surface of the end-use product over an extended lifetime. Typically, the end-use resin composition contains between about 0.1 and about 5 wt. percent of the water-soluble resin. Preferably, the end-use resin composition contains no more than about 1 wt. percent of the water-soluble resin.

Examples of the types of microbicidal compounds which may be employed in this invention include, but are not limited to, phenoxarsines (including bisphenoxarsines), phenarsazines (including bisphenarsazines), maleimides, isoindole dicarboximides having a sulfur atom bonded to the nitrogen atom of the dicarboximide group, halogenated aryl alkanols and isothiazolinone compounds.

The microbicidal phenoxarsine and phenarsazine compounds useful in the compositions of this invention include compounds represented by the formulas:

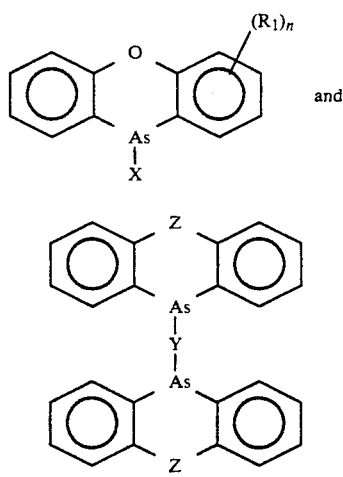

where X is halogen or thiocyanate, Y is oxygen or sulfur, Z is oxygen or nitrogen, R is halo or lower alkyl, and n is 0 to 3. Examples of these phenoxarsines and phenarsazines include, but are not limited to, 10-chlorophenoxarsine; 10-iodophenoxarsine; 10-bromophenoxarsine; 4-methyl-10-chlorphenoxarsine, 2-tert-butyl-10-chlorophenoxarsine; 1,4-dimethyl-10-chlorophenoxarsine; 2-methyl-8,10-dichlorophenoxarsine; 1,3,10-trichlorophenoxarsine; 2,6,10-trichlorophenoxarsine; 1,2,4,10-tetrachlorophenoxarsine; 10,10'-oxybisphenoxarsine (OBPA); 10,10'-oxybisphenarsazine and 10,10'-thiobisphenarsazine.

The microbicidal maleimide compounds useful in the compositions of this invention by a preferred maleimide, N-(2-methylnaphthyl) maleimide.

The microbicidal compounds useful in the practice of this invention which are isoindole dicarboximides having a sulfur atom bonded to the nitrogen atom of the dicarboximide group are compounds which contain at least one group having the structure:

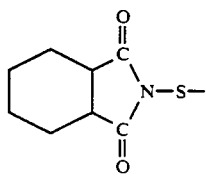

The preferred isoindole dicarboximides are the following:

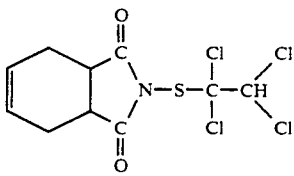

bis-[(1,1,2,2-tetrachloroethyl)thio]-4-cyclohexene-1,2-dicarboximide;

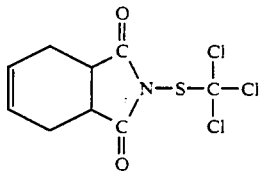

N-trichloromethylthio-4-cyclohexene-1,2-dicarboximide;

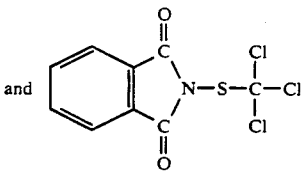

N-trichloromethylthio phthalimide.

The halogenated aryl alkanols which can be used as microbicidal compounds in accordance with this invention are exemplified by a preferred compound, 2,4-dichlorobenzyl alcohol.

An example of a preferred isothiazolinone compound useful in the composition of this invention is 2-(n-octyl-4-isothiazolin-3-one).

The most preferred microbicidal compounds are the bisphenoxarsines and bisphenarsazines having the formula:

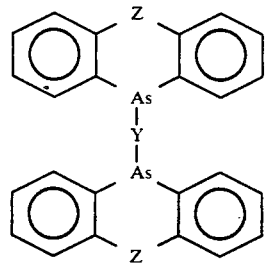

where Y is oxygen or sulfur and Z is oxygen or nitrogen. Of these bisphenoxarsines and bisphenarsazines, the most preferred are 10,10'-oxybisphenoxarsine, 10,10'-thiobisphenoxarsine; 10,10'-oxybisphenarsazine; and 10,10'-thiobisphenarsazine.

It is generally possible to incorporate at least about 1 wt %, more preferably 2 wt. %, of a bisphenoxarsine or bisphenarsazine in PVA-based, internally or externally plasticized, thermoplastic resin compositions. Using the preferred copolymer of vinyl alcohol and (alkyleneoxy)acrylate described in the above-referenced U.S. Pat. No, 4,618,648, it is possible to obtain up to about 5 wt. % compositions of phenarsazines and phenoxarsines dissolved in the solidified resin.

Concentrates containing up to about 20 wt. percent of phenarsazines and phenoxarsines are obtainable with the poly(alkyleneoxy) acrylate resin which dissolves such concentrations when molten: however, upon solidification of the resin, the microbicide comes out of solution as microcrystals suspended in the solidified resin.

Material comprising microbicides in water-soluble thermoplastic resin can also be used, for example, in agriculture or to protect a body of water, where a slow release of a microbicide due to the action of water is desired. The rate may be slowed even further by admixing, e.g., by melt-blending, the water-soluble concentrate with a water-insoluble resin. Unlike the case where the end-use product desirably contains only a minor amount of the water-soluble concentrate, a slow-release system may contain the water-soluble resin over a very wide percentage range, e.g., from 100 wt percent of the water-soluble resin of the concentrate to about 5 wt. %. For control of the rate of release, generally, at least about 5 wt. % of a water-insoluble polymer is required, more preferably at least about 20 wt. %. Generally, such a system will contain no more than about 80 wt. % of the water-insoluble resin, lest microbicide release become extremely low. (The weight percentages in this paragraph define the relative proportions of water-soluble and water-insoluble polymer; the weight of the microbicide being a relatively minor portion of the weight of a slow-release system.)

As a slow-release system is an end-use application of the microbicide, the concentration of microbicide may vary over a very extended range. Generally, the slow release material will contain at least 0.01 phr microbicide, preferably at least 0.1 phr, but may contain up to the limit which may be incorporated by dissolving the microbicide in molten resin.

A very surprising and unexpected aspect of the present invention is that microbicides heretofore incompatible with aqueous systems can be stably dispersed into aqueous systems through use of the concentrates. A number of commonly used microbicides, particularly the phenarsazines and phenoxarsines, are insoluble in water, and furthermore are not known to form stable dispersions in water. It is found that a number of such microbicides can be incorporated into water-soluble resins as described above as true solid solutions of the microbicides in the water-soluble resins. When such concentrates are added to water or an aqueous solution, the water-soluble polymer dissolves. The microbicide which had been dissolved in the water-soluble resin is precipitated, yet the precipitate from the concentrate is so finely divided that it remains as a stable dispersion in the water or aqueous solution.

Water-stable dispersions of microbicides have a wide range of utility. For example, they may be used as a vehicle for imparting the microbicide to fabric, such as that which is expected to be exposed to the elements and subject to mildew, etc. Water-stable dispersions may be added to water-based paints, coatings and adhesives to impart biocidal properties thereto.

For preparing aqueous dispersions of a water-insoluble microbicide, it is generally desirable that the microbicide be as concentrated relative to the water-soluble resin as possible. Any effect of the resin on potential end-use applications may be unpredictable, and it is therefore generally undesirable to add large amount of the resin in order to add the requisite amount of biocide. In some cases, the water-soluble resin may actually serve a purpose. For example, polyvinyl alcohol is a commonly used size for textile yarns, and a composition of PVA (or a PVA-based thermoplastic resin composition) and a microbicide may both size the yarns and impart biocidal characteristics thereto. However, even where the water-soluble resin itself has end-use utility, it is desirable to form concentrates and add such concentrates to additional water-soluble resin, because there is a cost of processing water-soluble resin with microbicides that is minimized by forming concentrates.

A currently useful prior art composition for imparting biological activity to an aqueous-based material, such as an aqueous latex, is as follows. A water-insoluble microbicide is dissolved in an oily liquid, such as a plasticizer. Using an appropriate dispersant or surfactant, the oily solution is emulsified into an aqueous medium. This material can then be added to aqueous-based compositions, such as latex paints.

The concentrates in accordance with the invention is advantageous in several respects over such prior art emulsions. To begin with, the concentrates of the present invention may be shipped in dry form and used to prepare dispersions, on site, within about 24 to 48 hours of use. Alternatively, the concentrates may be added directly to an aqueous system, whereupon the dispersion of the microbicide is created in situ. Dry shipping is inherently a cost saving over shipping considerable volumes of water, as is the case with emulsions. Dry shipping facilitates containment of any accidental spill. Until added to an aqueous system, the concentrates have an indefinite shelf-life; whereas emulsions tend to eventually settle, and the settled material may be difficult to reemulsify. Also in an emulsion, there may be crystal growth of the microbicide, whereupon gravity effects increase over time. An emulsion must also generally be protected during shipping and storage against freezing. All of the inherent disadvantages of emulsions are overcome with solid concentrate material useful for forming relatively stable microbicide dispersions on-site.

The dispersions which are produced when the concentrates of the present invention are dissolved in water or an aqueous medium are believed to be stabilized by the extremely small particle size of the microbicide dispersion and by the carrier resin. The carrier resin inherently increases the viscosity of the water or aqueous medium and slows settling of the microcrystals. Concentrates in which the microbicide is fully dissolved in the solidified carrier resin as well as those in which the microbicide is partially recrystallized in the solidified carrier resin are all suitable for forming dispersions according to the invention.

It is to be noted that when the concentrate contains a carrier resin having free hydroxyl groups, as is the case with PVA and PVA-based resins, a dispersion prepared therefrom will tend to thicken latexes containing free carboxylic acid groups. This may be disadvantageous. However, many such carboxylic acid-containing latex compositions, such as paints, contain thickeners, and any disadvantage of thickening may be compensated by appropriately adjusting the level of thickener added. Many latexes not having free carboxylic acid groups, on the other hand, are not thickened by hydroxyl group-containing carrier resins, and dispersions prepared in accordance with the invention may be used with such latex compositions without substantial modification of the formulation.

Concentrates of microbicides in water-soluble resins or mixtures of end-use resins may themselves be used to form end-use products that are useful for adding the microbicides to aqueous systems. For example, concentrates may be produced in film form and manufactured into water-soluble bags for use in commercial laundries. It is presently conventional in commercial laundries to add water-soluble bags containing detergents, microbicides, water softeners, etc. It may be readily appreciated that the addition of powdered microbicides to the detergent, water softener, etc., is an inherently hazardous operation. Likewise, inadvertent breakage of the bag, either at the laundry or throughout the distribution system poses a potential danger to those who might inadvertently come into contact with the hazardous mixture—probably without awareness of any such hazard. A water-soluble bag for detergents etc., in which the microbicide is dissolved in the bag material itself, greatly minimizes any potential hazard.

The invention will now be described in greater detail by way of specific examples.

EXAMPLE 1

Concentrates of 1%, 2% and 5% OBPA in Vinex 2025 copolymer of vinyl alcohol and (alkyleneoxy) acrylate were prepared. The Vinex 2025 was first ground using a Brinkman Mill equipped with a 4 mm screen. The Vinex granules were blended with the OBPA in a Hobart blender. The blends were then compounded using a 0.75 inch single screw extruder. The compounds processed best with extrusion temperatures of zone 1 at 165° C. zone 2 at 170° C., zone 3 at 175° C. and the die at 180° C. The extruder was equipped with a 4 inch wide sheet die. The concentrate sheets were granulated using the Brabender granulator equipped with a 4 mm screen.

Four rigid polymer resins were used in this example.

---

1. ABS.
2. Polycarbonate (PC).
3. PET from Hoechst Celanese.

The biological test procedures are described in Table 1 below.

TABLE 1

Biological Test on Extruded Films

| Polymer | Vinex (%) | OBPA (ppm) | Average* Zone of Inhibition (mm)/ Growth in Contact Area | | Growth of Rhodotorula rubra in agar overlay |
|---|---|---|---|---|---|
| | | | Staphylococcus aureus | Kubsiella pneumoniae | |
| ABS | 0 | 0 | 0/GCA | 0/GCA | HG |
| ABS | 1 | 500 | 0/GCA | 0/GCA | MG |
| ABS | 2.5 | 500 | 1/NGCA | 0/GCA | LG |
| ABS | 5 | 500 | 3/NGCA | 0/GCA | NG |
| PC | 0 | 0 | 0/GCA | 0/GCA | HG |
| PC | 1 | 500 | 0/GCA | 0/GCA | HG |
| PC | 2.5 | 500 | Halo/NGCA | 0/NGCA | NG |
| PC | 5 | 500 | 4/NGCA | 2/NGCA | NG |
| PET | 0 | 0 | 0/GCA | 0/GCA | HG |
| PET | 1 | 500 | 0/GCA | 0/GCA | MG |
| PET | 2.5 | 500 | 0/GCA | 0/GCA | TG |
| PET | 5 | 500 | Halo/NGCA | 0/GCA | NG |
| PS | 0 | 0 | 0/GCA | 0/GCA | HG |
| PS | 1 | 500 | Halo/NGCA | 0/GCA | NG |
| PS | 2.5 | 500 | 5/NGCA | 2/NGCA | NG |
| PS | 5 | 500 | 8/NGCA | 3/NGCA | NG |

*Average of 3 determinations
HG = Heavy growth
MG = Medium growth
LG = Light growth
TG = Trace growth
NG = No growth
CA = Contact area
Halo = Area of inhibited growth This resin is used to make polyester fibers.
4. Polystyrene (PS) PS-208.
A general purpose crystalline polystyrene resin from Huntsman Chemical.

Four films were prepared from each rigid polymer film using the three Vinex concentrates. Each of these films contained 500 ppm OBPA and 1%, 2½% or 5% of Vinex. An untreated control film of each resin was also prepared. Films were prepared on a single screw extruder equipped with a 4 inch sheet die. Extruder conditions are given below:

| Extrusive Condition for Rigid Films | | | | |
|---|---|---|---|---|
| | ABS | PC | PET | PS |
| Zone 1 (°C.) | 180 | 270 | 270 | 190 |
| Zone 2 (°C.) | 185 | 260 | 260 | 195 |
| Zone 3 (°C.) | 190 | 250 | 250 | 200 |
| Die (°C.) | 200 | 245 | 245 | 200 |
| Screw Speed (RPM) | 125 | 125 | 125 | 125 |

The extruded films were evaluated for activity against microorganisms.

Results

The 1% OBPA in Vinex 2025 processed well. The 2% OBPA in Vinex 2025 processed acceptably but some slippage of the compound on the extruder screw resulted in lower output The 5% OBPA in Vinex 2025 processed poorly with slippage of the compound on the extruder screw resulting in a loud squeaking sound and erratic output.

The addition of the Vinex did not affect the processing of the ABS, PC or PS films. The PET samples containing Vinex had to be extruded at a lower temperature than the virgin resin because of a loss of hot strength of the film. They processed well at the lower temperature. The addition of Vinex to PC and PS caused them to become slightly opaque.

This example demonstrates that Vinex is effective in improving the migration of OBPA through rigid polymers.

EXAMPLE 2

This test was done to determine the effects of a water-soluble carrier resin on the physical properties of a righd end-use resin. No microbicide was included because only physical properties were measured in this example.

Films of ABS (Cycolac T 4500) containing 0, 1, 5, 10 and 20% Vinex 2025 were prepared on a lab extruder. Cycolac T is the most widely used grade of general purpose ABS offered by General Electric. According to the manufacturer it is recognized as the standard of the ABS industry.

Blends containing 0, 1, 5, 10 and 20% Vinex 2025 in Cycolac T 4500 were made in the Hobart blender. Films were extruded from the blends on a 0.75 inch single screw extruder equipped with a 4 inch sheet die. They were cooled and polished on chrome rolls. The films were 20 to 25 mils thick.

The tensile strength was measured according to ASTM test method D 638 using a Type IV specimen and a crosshead speed of 5 mm/min.

The addition of the Vinex to the ABS had no effect on the processability of the films. The films containing 10% and 20% vinex had a laminar appearance when they were cut. The film with 5% Vinex showed this phenomena to a very slight extent. The Vinex is believed not to be miscible with the ABS and is believed to form a dispersed phase within the ABS continuous phase.

Table 2 contains the tensile strength measurements of the films. At up to 10% Vinex there is very little loss of physical properties. At 20% Vinex the loss in tensile is greater than 20%.

TABLE 2

Tensile Strength of Cycolac T with Vinex 2025

| % Vinex | Tensile Strength (psi) + S.D. | % Tensile Strength Loss |
| --- | --- | --- |
| 0 | 5970 + 180 | 0.0 |
| 1 | 5410 + 280 | 9.4 |
| 5 | 5530 + 140 | 7.3 |
| 10 | 5740 + 430 | 3.9 |
| 20 | 4570 + 190 | 23.5 |

EXAMPLE 3

5% OBPA concentrates in Vinex were prepared by extrusion and pelletizing to form small cylinders (⅛" diameter ⅛" height). The pellets were dissolved in various commercial latexes. The time of dissolving (in some cases), biological activity and thickening was determined. The results are given in Table 3 below:

TABLE 3

| Latex | Solubilizing Time | Thickens |
| --- | --- | --- |
| Acrylics | | |
| R&H Rhoplex E-31 | 1 hour | yes-slightly |
| R&H Rhoplex WL-91 | * | No |
| R&H Rhoplex TR-407 | * | No |
| R&H Rhoplex HA-16 | * | No |
| R&H Rhoplex NW-1402 | * | No |
| R&H Rhoplex K-3 | * | No |
| NS&C #78-6210 | * | No |
| NS&C #25-4280 | * | No |
| Morton-Lucidene 432 | * | No |
| Morton-Lucidene 243 | * | No |
| Morton-Lucidene 604 | * | No |
| Morton-Lucidene Polycryl 150-B | * | No |
| Morton-Lucidene Polycryl 7F-7 | * | No |
| SBR (styrene/butadiene rubbers) | | |
| D.G.-Genflo-3049 | | No |
| D.G.-Genflo-3000 | >1 hour | Yes |
| Reichold-Tylac- | 2 hours | Yes |
| EVA (ethylene vinyl acetate) | | |
| Air Products-Airflex TL-30 | >1 hour | Yes |
| Air Products-Flexbond TL-35 | * | No |
| PVDC (polyvinylidine chloride) | | |
| B. F. Goodrich-Geon 650X18 | >1 hour | Yes |

*A preformed dispersion was added to these samples
All samples exhibited biological activity While the invention has been described in terms of certain preferred embodiments, modifications obvious to one with ordinary skill in the art may be made without departing from the scope of the present invention.

Various features of the invention are set forth in the following claims.

What is claimed is:

1. A solid, melt-blended solution consisting essentially of a microbicide dissolved in a carrier resin that is a copolymer of vinyl alcohol and (alkyleneoxy) acrylate and is soluble in water to at least about 1 gm. per 100 ml. of water at 25° C., said solid solution being useful as a melt-processable additive to a primary rigid, non-plasticized, water-insoluble thermoplastic resin composition to impart biocidal activity thereto, said solid solution containing said microbicide at a level that is at least about 20 times higher than the normal end-use microbicide concentration in a primary rigid, non-plasticized, water-insoluble thermoplastic resin composition, said water-soluble thermoplastic carrier resin enabling said microbicide to impart improved antimicrobial activity to a rigid, non-plasticized, water-insoluble primary thermoplastic resin composition relative to the ability of water-insoluble thermoplastic carrier resins, at similar levels in a rigid, non-plasticized water-insoluble primary thermoplastic resin composition, to enable said microbicide to impart antimicrobial activity to a rigid, non-plasticized, water-insoluble primary thermoplastic resin composition.

2. A solid solution according to claim 1 wherein said microbicide is present at a level at least about 100 times the normal end-use level in a rigid primary thermoplastic resin composition.

3. A solid solution according to claim 1 wherein said microbicide is a water-insoluble microbicide.

4. A solid solution according to claim 1 wherein said microbicide is a phenoxarsine or a phenarsazine.

5. A solid solution according to claim 4 wherein said microbicide is 10,10'-oxybisphenoxarsine.

6. A solid solution according to claim 4 wherein said phenoxarsine or phenarsazine comprises at least about 1 wt. % of said solid solution.

7. A solid solution according to claim 4, wherein said phenoxarsine or phenarsazine comprises at least about 5 wt. % of said solid solution.

8. A solid solution according to claim 1 wherein said microbicide is an anti-microbial maleimide.

9. A solid solution according to claim 1 wherein said microbicide is an anti-microbial isoindole dicarboximide.

10. A solid solution according to claim 1 wherein said microbicide is an anti-microbial halogenated aryl alkanol.

11. A solid solution according to claim 1 wherein said microbicide is an anti-microbial isothiazolinone.

12. A solid, melt-blended solution consisting essentially of a water-insoluble microbicide dissolved in a carrier resin that is a copolymer of vinyl alcohol and (alkyleneoxy) acrylate and is soluble in water to at least about 1 gm. per 100 ml. of water at 25° C., said microbicide comprising at least about 0.01 wt. % of said solid solution, said solid solution when placed in an aqueous medium forming a dispersion of said water-insoluble microbicide in which said carrier resin stabilizes said dispersion.

13. A solid solution according to claim 12 wherein said microbicide is a phenoxarsine or a phenarsazine.

14. A solid solution according to claim 12 wherein said microbicide is 10,10'-oxybisphenoxarsine.

15. A solid solution according to claim 12 wherein said microbicide is an anti-microbial maleimide.

16. A solid solution according to claim 12 wherein said microbicide is an anti-microbial isoindole dicarboximide.

17. A solid solution according to claim 12 wherein said microbicide is an anti-microbial halogenated aryl alkanol.

18. A solid solution according to claim 12 wherein said microbicide is an anti-microbial isothiazolinone.

19. A solid solution according to claim 12 wherein said microbicide comprises at least about 1 wt. % of said solid solution.

* * * * *